United States Patent [19]

Ushioda et al.

[11] Patent Number: 4,895,671

[45] Date of Patent: Jan. 23, 1990

[54] OPTICALLY ACTIVE PHENYLPYRIMIDINE COMPOUND AND A LIQUID CRYSTAL COMPOSITION

[75] Inventors: Makoto Ushioda; Kouji Ohno; Shinichi Saito, all of Kanagawa, Japan

[73] Assignee: Chisso Corporation, Ohsaka, Japan

[21] Appl. No.: 260,986

[22] Filed: Oct. 21, 1988

[30] Foreign Application Priority Data

Oct. 21, 1987 [JP] Japan .................. 62-265933

[51] Int. Cl.[4] .............. G02F 1/13; C09K 19/34; C07D 239/02
[52] U.S. Cl. ................ 252/299.61; 252/299.01; 252/299.5; 350/350 R; 350/350 S; 544/298
[58] Field of Search ........... 252/299.61, 299.5, 299.01; 350/350 R, 350 S; 544/298

[56] References Cited

U.S. PATENT DOCUMENTS

| | | | |
|---|---|---|---|
| 4,725,688 | 2/1988 | Taguchi et al. | 252/299.61 |
| 4,765,924 | 8/1988 | Inoue et al. | 252/299.61 |
| 4,784,792 | 11/1988 | Inoue et al. | 252/299.61 |
| 4,784,793 | 11/1988 | Coates et al. | 252/299.61 |
| 4,786,730 | 11/1988 | Shibata et al. | 252/299.61 |
| 4,804,759 | 2/1989 | Shibata et al. | 252/299.61 |
| 4,824,597 | 4/1989 | Kano | 252/299.61 |
| 4,831,143 | 5/1989 | Shibata et al. | 252/299.61 |
| 4,834,904 | 5/1989 | Krause et al. | 252/299.61 |
| 4,835,274 | 5/1989 | Kano | 252/299.61 |

FOREIGN PATENT DOCUMENTS

| | | |
|---|---|---|
| 225195 | 6/1987 | European Pat. Off. ........ 252/299.61 |
| 260077 | 3/1988 | European Pat. Off. ........ 252/299.61 |
| 284008 | 9/1988 | European Pat. Off. ........ 252/299.61 |
| 2257588 | 6/1973 | Fed. Rep. of Germany ........ 252/299.61 |
| 3515373 | 11/1986 | Fed. Rep. of Germany ........ 252/299.61 |
| 3709618 | 10/1988 | Fed. Rep. of Germany ........ 252/299.61 |
| 62209190 | 9/1987 | Japan ........ 252/299.61 |
| 6337186 | 2/1988 | Japan ........ 252/299.61 |

OTHER PUBLICATIONS

Goodby, J. W., et al., Liquid Crystals and Ordered Fluids, vol. 4, Griffin A. C., et al., Ed., Plenum Press, N.Y., pp. 1–32 (1985).

Primary Examiner—Teddy S. Gron
Attorney, Agent, or Firm—Wenderoth, Lind & Ponack

[57] ABSTRACT

An optically active liquid crystal compound useful as a component of ferroelectric liquid crystal compositions and exhibiting ferroelectric properties within a broad temperature region including room temperature and a liquid crystal composition containing the compound are provided, which compound is an optically active phenylpyrimidine compound expressed by the formula

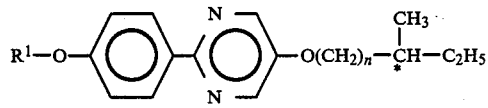

wherein $R^1$ is a 1–18C alkyl group, n is an integer of 2–15 and C having * attached thereonto indicates an asymmetric carbon atom.

13 Claims, No Drawings

OPTICALLY ACTIVE PHENYLPYRIMIDINE COMPOUND AND A LIQUID CRYSTAL COMPOSITION

BACKGROUND OF THE INVENTION

1. Field of the Invention

This invention relates to a novel liquid crystal compound having an optically active group and a liquid crystal composition containing the same. More particularly it relates to an optically active phenylpyrimidine compound useful as a component of ferroelectric liquid crystal compositions and a ferroelectric liquid crystal composition containing the compound.

2. Description of the Related Art

At present, TN (Twisted Nematic) display mode has been most broadly employed. This TN liquid crystal display has a number of advantages such as low driving voltage, small power consumption, etc., but it is inferior in the aspect of response rate to emissive mode display elments such as cathode rays tube display, electroluminescence display, plasma display, etc. A new TN mode display element having a twist angle enlarged to 180°–270° has also been developed, but it is also inferior in the aspect of response rate. Various efforts for improvement have been made, but a liquid crystal element having a high response rate has not been realized. However, in the case of a new display mode using ferroelectric liquid crystals, which mode has recently been extensively researched, there is a possibility of notably improving the response rate (Clark et al, Applied, Phys. Lett., 36, 899 (1980)). This display mode is directed to a method utilizing chiral smectic phases such as chiral smectic C phase (hereinafter abbreviated to SC*). Phases exhibiting ferroelectric properties are not limited only to SC* phase, but it is known that chiral smectic F, G, H, I and the like phases exhibit ferroelectric properties. When these ferroelectric liquid crystals are utilized for display elements, liquid crystal materials exhibiting ferroelectric liquid crystal phases in a broad temperature range including room temperature have been desired. At present, however, no single compound which satisfies such a requirement has been known; hence liquid crystal compositions obtained by combining some compounds to thereby satisfy the required specific feature as much as possible have been used.

SUMMARY OF THE INVENTION

The object of the present invention is to provide an optically active liquid crystal compound useful as a component of liquid crystal compositions suitable to the above-mentioned display mode and exhibiting ferroelectric properties in a broad temperature region including room temperature, and a liquid crystal composition containing the liquid crystal compound.

The present invention resides in:

an optically active phenylpyrimidine compound expressed by the formula

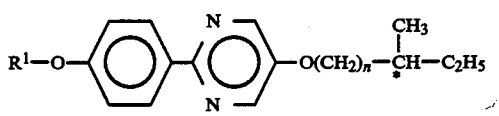

wherein $R^1$ represents an alkyl group of 1 to 18 carbon atoms, n represents an integer of 2 to 15 and C having * attached thereonto indicates an asymmetric carbon atom, and a liquid crystal composition containing the compound.

DETAILED DESCRIPTION OF PREFERRED EMBODIMENTS

Representative examples of the compound of the formula (I) are shown below.

5-(3-Methylpentyloxy)-2-(4-pentyloxyphenyl)pyrimidine, 2-(4-Hexyloxyphenyl)-5-(3-methylpentyloxy)pyrimidine, 2-(4-Heptyloxyphenyl)-5-(3-methylpentyloxy)pyrimidine, 5-(3-Methylpentyloxy)-2-(4-octyloxyphenyl)pyrimidine, 5-(3-Methylpentyloxy)-2-(4-nonyloxyphenyl)pyrimidine, 2-(4-Decyloxyphenyl)-5-(3-methylpentyloxy)pyrimidine, 5-(3-Methylpentyloxy)-2-(4-undecyloxyphenyl)pyrimidine, 2-(4-Dodecyloxyphenyl)-5-(3-methylpentyloxy)pyrimidine, 5-(4-Methylhexyloxy)-2-(4-pentyloxyphenyl)pyrimidine, 2-(4-Hexyloxyphenyl)-5-(4-methylhexyloxy)pyrimidine, 2-(4-Heptyloxyphenyl)-5-(4-methylhexyloxy)pyrimidine (compound No. 3), 5-(4-Methylhexyloxy)-2-(4-octyloxyphenyl)pyrimidine, 5-(4-Methylhexyloxy)-2-(4-nonyloxyphenyl)pyrimidine (compound No. 6)

2-(4-Decyloxyphenyl)-5-(4-methylhexyloxy)pyrimidine, 5-(4-Methylhexyloxy)-2-(4-undecyloxyphenyl)pyrimidine, 2-(4-Dodecyloxyphenyl)-5-(4-methylhexyloxy)pyrimidine, 5-(5-Methylheptyloxy)-2-(4-pentyloxyphenyl)pyrimidine, 2-(4-Hexyloxyphenyl)-5-(5-methylheptyloxy)pyrimidine (compound No. 2), 2-(4-Heptyloxyphenyl)-5-(5-methylheptyloxy)pyrimidine, 5-(5-Methylheptyloxy)-2-(4-octyloxyphenyl)pyrimidine, 5-(5-Methylheptyloxy)-2-(4-nonyloxyphenyl)pyrimidine, 2-(4-Decyloxyphenyl)-5-(5-methylheptyloxy)pyrimidine (compound No. 7), 5-(5-Methylheptyloxy)-2-(4-undecyloxyphenyl)pyrimidine, 2-(4-Dodecyloxyphenyl)-5-(5-methylheptyloxy)pyrimidine, 5-(6-Methyloctyloxy)-2-(4-pentyloxyphenyl)pyrimidine (compound No. 1), 2-(4-Hexyloxyphenyl)-5-(6-methyloctyloxy)pyrimidine, 2-(4-Heptyloxyphenyl)-5-(6-methyloctyloxy)pyrimidine, 5-(6-Methyloctyloxy)-2-(4-octyloxyphenyl)pyrimidine, 5-(6-Methyloctyloxy0-2-(4-nonyloxyphenyl)pyrimidine, 2-(4-Decyloxyphenyl)-5-(6-methyloctyloxy)pyrimidine, 5-(6-Methyloctyloxy)-2-(4-undecyloxyphenyl)pyrimidine, 2-(4-Dodecyloxyphenyl)-5-(6-methyloctyloxy)pyrimidine, 5-(7-Methylnonyloxy)-2-(4-pentyloxyphenyl)pyrimidine,
2-(4-Hexyloxyphenyl)-5-(7-methylnonyloxy)pyrimidine,
2-(4-Heptyloxyphenyl)-5-(8-methylnonyloxy)pyrimidine (compound No. 4),
5-(7-Methylnonyloxy)-2-(4-octyloxyphenyl)pyrimidine,
5-(7-Methylnonyloxy)-2-(4-nonyloxyphenyl)pyrimidine,
2-(4-Decyloxyphenyl)-5-(7-methylnonyloxy)pyrimidine,
5-(7-Methylnonyloxy)-2-(4-undecyloxyphenyl)pyrimidine,
2-(4-Dodecyloxyphenyl)-5-(7-methylnonyloxy)pyrimidine,
5-(8-Methyldecyloxy)-2-(4-pentyloxyphenyl)pyrimidine,
2-(4-Hexyloxyphenyl)-5-(8-methyldecyloxy)pyrimidine,
2-(4-Heptyloxyphenyl)-5-(8-methyldecyloxy)pyrimidine,
5-(8-Methyldecyloxy)-2-(4-octyloxyphenyl)pyrimidine (compound No. 5),
5-(8-Methyldecyloxy)-2-(4-nonyloxyphenyl)pyrimidine,
2-(4-Decyloxyphenyl)-5-(8-methyldecyloxy)pyrimidine,
5-(8-Methyldecyloxy)-2-(4-undecyloxyphenyl)pyrimidine,
2-(4-Dodecyloxyphenyl)-5-(8-methyldecyloxy)pyrimidine.

The phase transition points of some of the representative compounds of the formula (I) are shown below in Table 1.

TABLE 1

| Compound No. | In formula (I) R¹ | n | Abs. conf. | Phase transition points (°C.) Cr | SC* | Ch | I | Note |
|---|---|---|---|---|---|---|---|---|
| 1 | C₅H₁₁ | 5 | S | • 56.3 | • 73.0 | • 74.5 | • | |
| 2 | C₆H₁₃ | 4 | S | • 55.1 | • 57.6 | • 70.6 | • | |
| 3 | C₇H₁₅ | 3 | S | • 65.8 | — | • 79.0 | • | |
| 4 | C₇H₁₅ | 6 | S | • 43.0 | • 75.5 | • 78.0 | • | |
| 5 | C₈H₁₇ | 7 | S | • 40.3 | • 87.2 | — | • | Example 1 |
| 6 | C₉H₁₉ | 3 | S | • 38.9 | • 57.0 | • 70.7 | • | |
| 7 | C₁₀H₂₁ | 4 | S | • 33.3 | • 58.0 | • 71.2 | • | |

Cr; crystalline phase,
Ch; cholesteric phase,
I; isotropic liquid,
abs. conf.; absolute configuration Most of the compounds of the formula (I) of the present invention exhibit liquid crystal phases, particularly SC* phase, and they can be not only singly used, but also used as a component of ferroelectric liquid crystal compositions. The compounds of the present invention are characterized for example in that they have SC* phase in a broad temperature range in the vicinity of room temperature and no higher-order smectic phase is present on the lower temperature side relative to SC* phase.

Among ferroelectric liquid crystal phases, SC* phase is a phase present in the highest temperature region, and hence it is an optimum phase used for ferroelectric liquid crystal display. A compound for which a higher-order smectic phase appears on the lower temperature side relative to SC* phase, has a drawback of notably raising the lower limit temperature of SC* phase, when the compound is used as a component of compositions. Since the compound of the present invention does not have such a higher-order smectic phase, the compound does not raise the lower limit temperature of SC* phase.

For example, a compound expressed by the formula

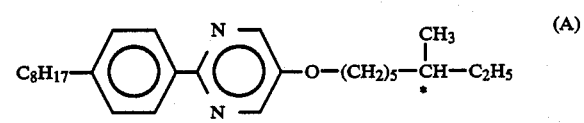

is disclosed in the 11th Liquid Crystal Discussion Meeting, preprints, 2N 18 (1985) (literature 1) and Japanese patent application laid-open No. Sho 61-215372/1986, and its phase transition points are as follows:

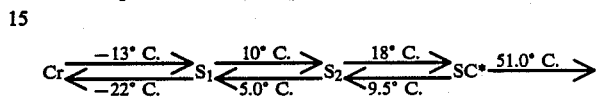

wherein S₁ and S₂ each show a smectic phase the attribution of which is unknown. When the phase transition points of this compound are compared with the phase transition points

of a compound of the present invention (compound No. 5 of Example 1) expressed by the formula

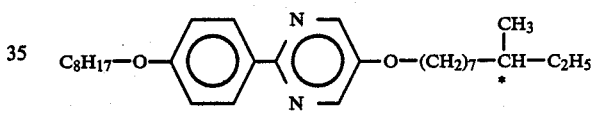

then it is seen that by replacing the alkyl group on the phenyl group by an alkoxy group, a notable effect is exhibited in that a higher-order smectic phase is extinguished and a temperature region exhibiting SC* phase is broadened.

Further, another compound disclosed in the above-mentioned literature (1), of the formula

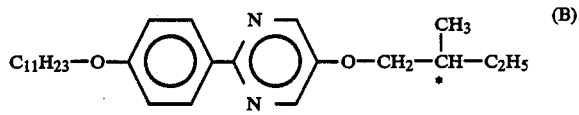

exhibits only a melting point of 51.0° C. The compound (B) corresponds to a compound of the present invention expressed by the formula (I) wherein R¹ represents C₁₁H₂₃ and n represents 1, but in the case of n=1, the compound does not exhibit not only SC* phase, but also even liquid crystal phases. The present inventors have investigated these facts and as a result have found that in the case of n≧2, liquid crystal phases appear and most of the compounds exhibit ferroelectric properties.

It is apparent from such comparison that the optically active compound expressed by the formula (I) is a far superior liquid crystal compound.

Although it is possible to singly use the compound of the formula (I) as a liquid crystal used for ferro-electric liquid crystal display elements, it is also possible to compose a ferroelectric liquid crystal composition from a plurality of the compounds of the formula (I) and further it is also possible to compose the composition from a mixture of at least one of the compounds of the formula (I) with other optically active or non-optically active smectic liquid crystal compound(s) or non-liquid crystal compound(s).

By adding to at least one of the compounds of the formula (I), a liquid crystal compound broadening the temperature region on the high temperature side and/or that on the lower temperature side, it is possible to obtain a more excellent ferroelectric liquid crystal composition for display elements.

Further, since the compound of the present invention has an optically active carbon atom, it has a capability of inducing a twist structure when it is added to a nematic liquid crystal. A nematic liquid crystal having a twist structure, i.e. a chiral nematic liquid crystal forms no reverse domain; hence the compound of the present invention can also be used as an agent for preventing the reverse domain from forming.

Racemates corresponding to the compound of the formula (I) of the present invention can be prepared in the same manner as in the preparation of the formula (I) by using raw materials for the racemates. The racemates exhibit almost the same phase transition and phase transition points as those of optically active substances corresponding to the racemates, but the racemates exhibit SC phase in place of SC* phase and nematic phase (hereinafter abbreviated to N phase) in place of Ch phase. These racemates may be used as an agent for adjusting the chiral pitch of these compounds.

The compound of the formula (I) can be prepared through the following route:

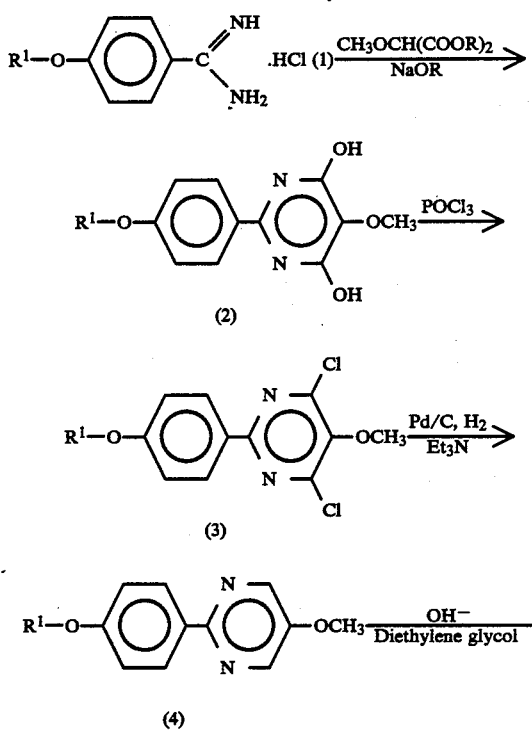

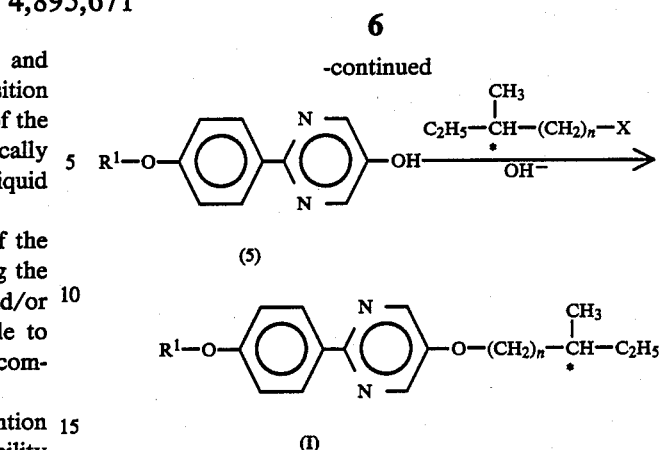

In the above equations, $R^1$ represents an alkyl group such as methyl, ethyl, etc. and X represents a group to be eliminated such as Cl, Br, I, p-toluenesulfonyloxy group, benzenesulfonyloxy group, methanesulfonyloxy group, etc.

Namely, a p-alkoxybenzamidine hydrochloride (1) is reacted with a methoxymalonic acid diester in the presence of a sodium alcoholate to obtain a diol (2), which is halogen-substituted with a halogenating agent such as phosphorus oxychloride to obtain a compound (3), which is dehalogenated in the presence of a base to obtain a compound (4), which is heat-treated in the presence of an alkali in diethylene glycol to obtain a compound (5), which is etherified to obtain a compound (I). Further, the compound of the formula (I) can also be prepared through the following route:

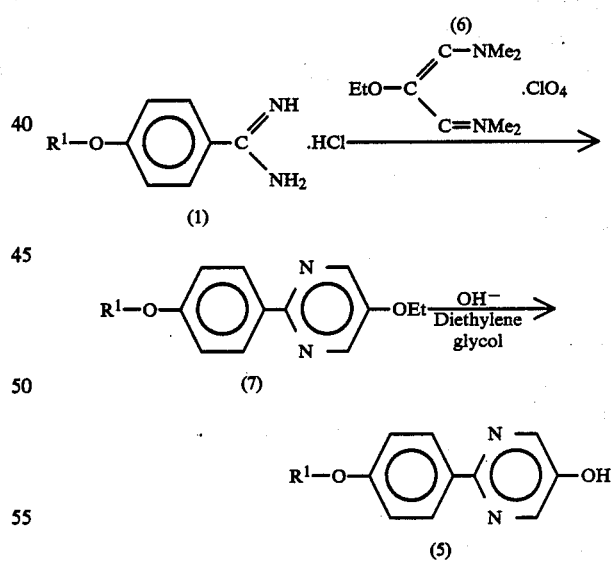

Namely, a compound (6) disclosed in the literature (Collection Czechoslov. Chem. Commun., 38 (1973), 1168) is reacted with a p-alkoxybenzamidine hydrochloride (1) in the presence of a sodium alcoholate to obtain a compound (7), which is treated with an alkali to obtain a compound (5). The subsequent step is carried out in the same manner as that described in the above-mmentioned route.

Further, the compond of the formula (I) can also be prepared through the following route:

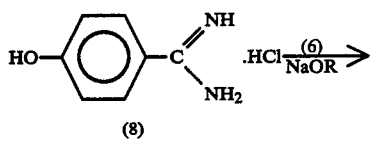

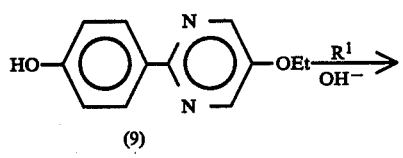

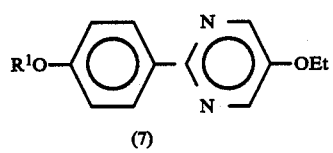

Namely, a compound (6) can be reacted with p-hydroxybenzamidine hydrochloride (8) in the presence of a sodium alcoholate to prepare a compound (9), which is etherified to prepare a compound (7). The subsequent step is carried out in the same manner as that of the above route to prepare the compound (I).

The compound and the liquid crystal composition of the present invention will be described in more detail by way of Examples.

EXAMPLE 1

Preparation of (S)-5-(8-methyldecyloxy)-2-(4-octyloxyphenyl)pyrimidine (a compound of the formula (I) wherein $R^1$ represents $C_8H_{17}$ and n represents 7)

(i) Preparation of 5-ethoxy-2-(4-hydroxyphenyl)pyrimidine p-Hydroxybenzamidine hydrochloride salt (200 g) and 1,3-bis(dimethylamino)-2-ethoxytrimethinium perchlorate (313.5 g) prepared in the same manner as that described in the literature (Collection Czechoslov. Chem. Commun., 38 (1973), 1168) were added to a solution of sodium methylate (194.6 g) in methanol (2,000 ml), followed by keeping the mixture under reflux for 6.5 hours, allowing the resulting material to cool down, adding water until the system became uniform, further adding acetic acid until the system was acidifed and filtering off deposited crystals to obtain 5-ethoxy-2-(4-hydroxyphenyl)pyrimidine (205 g, m.p.: 201.5°–202.3° C.).

(ii) Preparation of 5-ethoxy-2-(4-octyloxyphenyl)pyrimidine

To a solution of 5-ethoxy-2-(4-hydroxyphenyl)pyrimidine (40 g) dissolved in ethanol (340 ml) were added potassium hydroxide (11.2 g) and octyl bromide (35.8 g), followed by keeping the mixture under reflux for 3 hours, distilling off ethanol (about 300 ml), extracting the residue with toluene (500 ml), washing the resulting organic layer with 2N—NaOH aqueous solution, further washing with water until the washing water became neutral, distilling off low boiling substances in the organic layer and recrystallizing the residue from ethanol to obtain 5-ethoxy-2-(4-octyloxyphenyl)pyrimidine (46.9 g). This product exhibited a phase transition of

(iii) Preparation of 5-hydroxy-2-(4-octyloxyphenyl)pyrimidine

NaOH (58.4 g) was added to a solution of 5-ethoxy-2-(4-octyloxyphenyl)pyrimidine (48 g) dissolved in diethylene glycol (300 ml), followed by keeping the mixture at 220° C. for 3 hours, allowing the resulting material to cool down, adding water and acetic acid, filtering off deposited crystals, and recrystallizing from ethanol to obtain 5-hydroxy-2-(4-octyloxyphenyl)pyrimidine (29 g, m.p.: 131.2°–132.5° C.)

(iv) Preparation of the captioned compound

KOH (0.8 g) was added to a solution of 5-hydroxy-2-(4-octyloxyphenyl)pyrimidine (4 g) dissolved in ethanol (20 ml), followed by adding (S)-8-methyldecyl bromide (3.2 g) prepared according to the method disclosed in the literature (Mol. Cryst. Liq. Cryst., 1984, Vol. 114, pp. 237–247), keeping the mixture under reflux for 6 hours, allowing the resulting material to cool down, extracting it with toluene, washing the resulting organic layer with 2N-NaOH aqueous solution, further washing with water until the washing water became neutral, distilling off low-boiling components in the organic layer and recrystallizing the residue from ethanol to obtain the captioned compound, (S)-5-(8-methyldecyloxy)-2-(4-octyloxyphenyl)pyrimidine (1.8 g). Its phase transition points were as follows:

EXAMPLE 2 (Use example 1)

A nematic liquid crystal composition consisting of

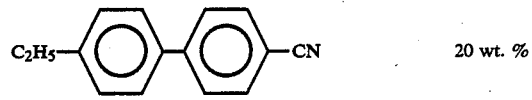  20 wt. %

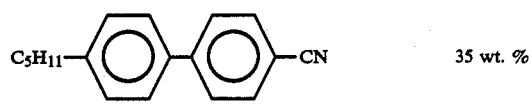  35 wt. %

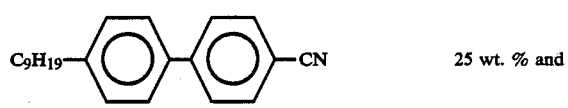  25 wt. % and

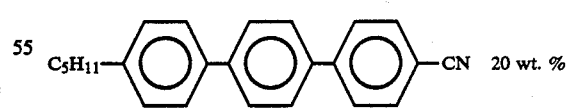  20 wt. % was filled in a cell provided with transparent electrodes each obtained by coating polyvinyl alcohol (PVA) as an aligning agent, followed by rubbing the resulting surface to subject it to a parallel aligning treatment and having a distance between the electrodes, of 10 μm to prepare a TN mode display cell, which was then observed under a polarizing microscope. As a result, a reverse domain was observed to be formed.

To this nematic liquid crystal composition was added compound No. 6 of the present invention,

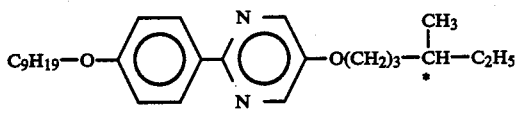

in an amount of 1% by weight, followed by observing the resulting composition in a similar TN mode cell. As a result, the reverse domain did not appear, and a uniform nematic phase was observed.

EXAMPLE 3 (Use example 2)

Compound No. 7 of the present invention in an amount of 1% by weight was added to a commercially available nematic liquid crystal composition, ZLI-1132 (tradename of product made by Merck Company), followed by measuring the chiral pitch of the resulting chiral nematic liquid crystal composition according to Cano-wedge method (see Applied Physics, 43 (2) 126–131 (1974)). The results were as follows:

| Temperature (°C.) | Pitch (μm) |
|---|---|
| 20 | 52.0 |
| 30 | 55.8 |
| 40 | 60.2 |
| 50 | 66.6 |
| 60 | 73.1 |

EXAMPLE 4 (Use example 3)

The following composition was prepared from compounds of the present invention:

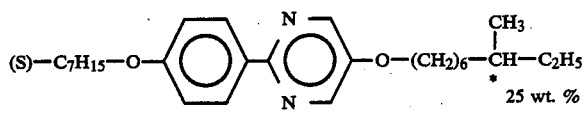
(No. 4)

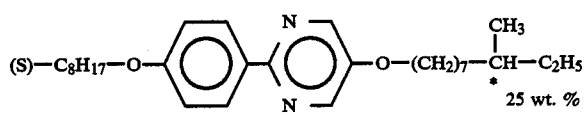
(No. 5)

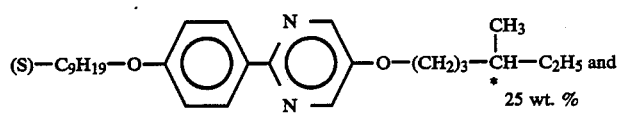
(No. 6)

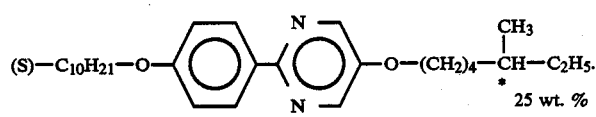
(No. 7)

The phase transition points of the above composition were as follows:

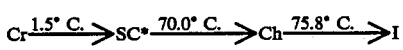

As apparent from the foregoing, when a plurality of the compounds of the present invention are combined together, it is possible to compose a ferroelectric liquid crystal composition in a broad temperature range including room temperature.

What we claim is:

1. An optically active phenylpyrimidine compound expressed by the formula

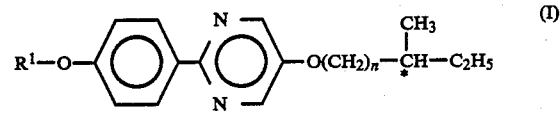

wherein n represents an integer of 3 to 7; when n is 3, $R^1$ represents alkyl of 8 to 12 carbon atoms; when n is 4, $R^1$ represents alkyl of 6 to 12 carbon atoms; when n is 5 to 7, $R^1$ represents alkyl of 5 to 12 carbon atoms; and the symbol * indicates an asymmetric carbon atom.

2. An optically active phenylpyrimidine compound according to claim 1, wherein n is 3.

3. An optically active phenylpyrimidine compound according to claim 1, wherein n is 4.

4. An optically active phenylpyrimidine compound according to claim 3, wherein $R^1$ represents alkyl of 6 or 10 carbon atoms.

5. An optically active phenylpyrimidine compound according to claim 1, wherein n is 5 to 7.

6. An optically active phenylpyrimidine compound according to claim 5, wherein $R^1$ represents alkyl of 5 to 11 carbon atoms.

7. An optically active phenylpyrimidine compound according to claim 5, wherein n is 6 and $R^1$ represents —$C_7H_{15}$.

8. An optically active phenylpyrimidine compound according to claim 5, wherein n is 7 and $R^1$ represents —$C_8H_{17}$.

9. A chiral nematic liquid crystal composition having an optically active phenylpyrimidine compound as set forth in claim 1 added to a nematic liquid crystal composition.

10. A chiral nematic liquid crystal composition according to claim 9, wherein said nematic liquid crystal composition consists of

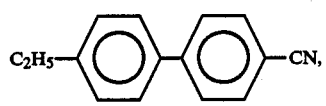

-continued

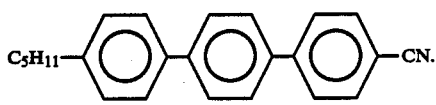

11. A ferroelectric liquid crystal composition having an optically active phenylpyrimidine compound as set forth in claim 1 blended with a smectic liquid crystal composition.

12. A liquid crystal composition comprising at least two different optically active phenylpyrimidine compounds expressed by the formula

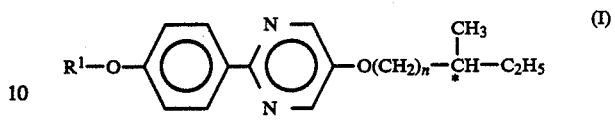

wherein n represents an integer of 3 to 7; when n is 3, $R^1$ represents alkyl of 8 to 12 carbon atoms; when n is 4, $R^1$ represents alkyl of 6 to 12 carbon atoms; when n is 5 to 7, $R^1$ represents alkyl of 5 to 12 carbon atoms; and the symbol * indicates an asymmetric carbon atom.

13. A liquid crystal composition according to claim 12, consisting of

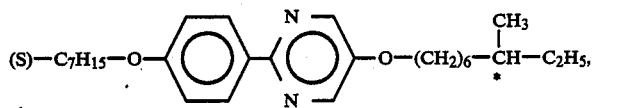

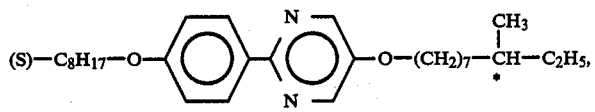

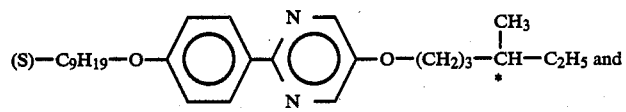

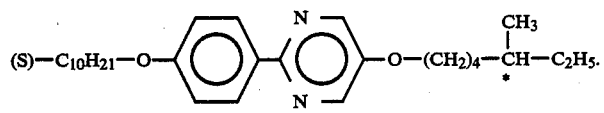

* * * * *